United States Patent
Wu et al.

(10) Patent No.: US 11,964,881 B2
(45) Date of Patent: Apr. 23, 2024

(54) METHOD FOR MAKING IRIDIUM OXIDE NANOPARTICLES

(71) Applicant: NATIONAL CHIAO TUNG UNIVERSITY, Hsinchu (TW)

(72) Inventors: Pu-Wei Wu, Zhubei (TW); Yi-Chieh Hsieh, Kaohsiung (TW); Han-Yi Wang, Taichung (TW); Kuang-Chih Tso, Kaohsiung (TW); Tzu-Ying Chan, Taoyuan (TW); Chung-Kai Chang, Taipei (TW); Chi-Shih Chen, Kaohsiung (TW); Yu-Ting Cheng, New Taipei (TW)

(73) Assignee: NATIONAL YANG MING CHIAO TUNG UNIVERSITY, Hsinchu (TW)

( * ) Notice: Subject to any disclaimer, the term of this patent is extended or adjusted under 35 U.S.C. 154(b) by 714 days.

(21) Appl. No.: 16/939,984

(22) Filed: Jul. 27, 2020

(65) Prior Publication Data

US 2021/0292187 A1    Sep. 23, 2021

(30) Foreign Application Priority Data

Mar. 18, 2020 (TW) .................................. 109109026

(51) Int. Cl.
| | | |
|---|---|---|
| *C01G 55/00* | (2006.01) | |
| *A61L 27/02* | (2006.01) | |
| *B82Y 30/00* | (2011.01) | |
| *B82Y 40/00* | (2011.01) | |

(52) U.S. Cl.
CPC .......... *C01G 55/004* (2013.01); *A61L 27/025* (2013.01); *B82Y 30/00* (2013.01); *B82Y 40/00* (2013.01); *C01P 2004/64* (2013.01)

(58) Field of Classification Search
None
See application file for complete search history.

(56) References Cited

U.S. PATENT DOCUMENTS

| | | |
|---|---|---|
| 7,976,989 B2 | 7/2011 | Lopez et al. |
| 8,211,388 B2 | 7/2012 | Woodfield et al. |
| 8,263,290 B2 | 9/2012 | Lopez et al. |

(Continued)

FOREIGN PATENT DOCUMENTS

| | | |
|---|---|---|
| CN | 104437481 A | 3/2015 |
| WO | 2012010501 A1 | 1/2012 |

OTHER PUBLICATIONS

Hsieh et al., Development of IrO2 bio-ink for ink-jet printing application, Ceramic International 45, 2019, 16645-16650, published May 21, 2019 (Year: 2019).*

(Continued)

*Primary Examiner* — Coris Fung
*Assistant Examiner* — Keling Zhang
(74) *Attorney, Agent, or Firm* — Lando & Anastasi, LLP

(57) ABSTRACT

A method for making iridium oxide nanoparticles includes dissolving an iridium salt to obtain a salt-containing solution, mixing a complexing agent with the salt-containing solution to obtain a blend solution, and adding an oxidating agent to the blend solution to obtain a product mixture. A molar ratio of a complexing compound of the complexing agent to the iridium salt is controlled in a predetermined range so as to permit the product mixture to include iridium oxide nanoparticles.

19 Claims, 9 Drawing Sheets

(56) References Cited

U.S. PATENT DOCUMENTS 9,695,521 B2   7/2017   Yanson et al.

OTHER PUBLICATIONS

Steegstra et al., Involvement of nanoparticles in the electrodeposition of hydrous iridium oxide films, Electrochimica Acta, 68, 2012, 206-213 (Year: 2012).*

Chen et al., Chemical bath deposition of IrO2 films on ITO substrate, Ceramics International, 40, 2014, 14983-14990 (Year: 2014).*

Y. Zhao, E.A. Hernandez-Pagan, N.M. Vargas-Barbosa, J.L. Dysart, T.E. Mallouk, "A High Yield Synthesis of Ligand-Free Iridium Oxide Nanoparticles with High Electrocatalytic Activity", The Journal of Physical Chemistry Letters, 2, pp. 402-406 (2011).

T.D. Nguyen, G.G. Scherer, Z.J. Xu, "A Facile Synthesis of Size-Controllable IrO2 and RuO2 Nanoparticles for the Oxygen Evolution Reaction", Electrocatalysis, 7, pp. 420-427 (2016).

Y. Lee, J. Suntivich, K.J. May, E.E. Perry, S.-H. Yang, "Synthesis and Activities of Rutile IrO2 and RuO2 Nanoparticles for Oxygen Evolution in Acid and Alkaline Solutions", The Journal of Physical Chemistry Letters, 3, pp. 399-404 (2012).

* cited by examiner

METHOD FOR MAKING IRIDIUM OXIDE NANOPARTICLES

CROSS-REFERENCE TO RELATED APPLICATION

This application claims priority from Taiwanese invention patent application no. 109109026, filed on Mar. 18, 2020.

FIELD

The disclosure relates to a method for making metal oxide, more particularly to a method for making iridium oxide nanoparticles.

BACKGROUND

Iridium oxide nanoparticles have advantages of high chemical stability, high electrochemical stability, high resistant to chemical corrosion, high electrocatalytic activity, and so on, and are widely used in, for example, solid polymer electrolyte batteries, fuel batteries, etc. In addition, iridium oxide nanoparticles have properties of superior biocompatibility and promoting growth of nerve cells, and may be used as a component of a bio-ink.

Yixin Zhao et al proposed a synthesis method of iridium oxide nanoparticles in an article entitled "A High Yield Synthesis of Ligand-Free Iridium Oxide Nanoparticles with High Electrocatalytic Activity," J. Phys. Chem. Lett., 2011, 2, 402-406. In this article, iridium oxide nanoparticles were obtained by hydrolyzing $IrCl_6^{2-}$ in base at 90° C. to produce $[Ir.(OH)_6]^{2-}$ and then treating with $HNO_3$ at 0° C. The acidified nanoparticles are stable for at least one month at 2° C. and can be used to make colloidal solutions between pH 1 and 13.

Youngmin Lee et al proposed another synthesis method of iridium oxide nanoparticles in an article entitled "Synthesis and Activities of Rutile $IrO_2$ and $RuO_2$ Nanoparticles for Oxygen Evolution in Acid and Alkaline Solutions," J. Phys. Chem. Lett., 2012, 3, 399-404. In this article, rutile $IrO_2$ nanoparticles were prepared by heating $IrCl_4 \cdot xH_2O$ precursor in the presence of a reducing agent to 200° C. in Ar atmosphere to obtain iridium nanoparticles, followed by thermal oxidation of the iridium nanoparticles at 500° C. in 0 2 atmosphere.

SUMMARY

An object of the disclosure is to provide a novel method for making iridium oxide nanoparticles by which the iridium oxide nanoparticles may be formed at room temperature in a more rapid way.

According to a first aspect of the disclosure, a method for making iridium oxide nanoparticles includes the steps of:
a) dissolving an iridium salt in a salt-dissolving solvent to obtain a salt-containing solution;
b) after step a), mixing a complexing agent with the salt-containing solution to obtain a blend solution, the complexing agent including a complexing compound which is for complexing iridium ions of the iridium salt, and which has a molar amount larger than that of the iridium salt; and
c) after step b), adding an oxidating agent to the blend solution so as to permit oxidation of the iridium ions, to thereby obtain a product mixture, the oxidating agent including an oxidant compound,
wherein a molar ratio of the complexing compound to the iridium salt is controlled in a predetermined range so as to permit the product mixture produced in step c) to include iridium oxide nanoparticles.

According to a second aspect of the disclosure, a bio-ink includes the iridium oxide nanoparticles made by the above method, and a dispersant for dispersing the iridium oxide nanoparticles.

BRIEF DESCRIPTION OF THE DRAWINGS

Other features and advantages of the disclosure will become apparent in the following detailed description of the embodiment (s) with reference to the accompanying drawings, in which.

DETAILED DESCRIPTION

Figure 1:
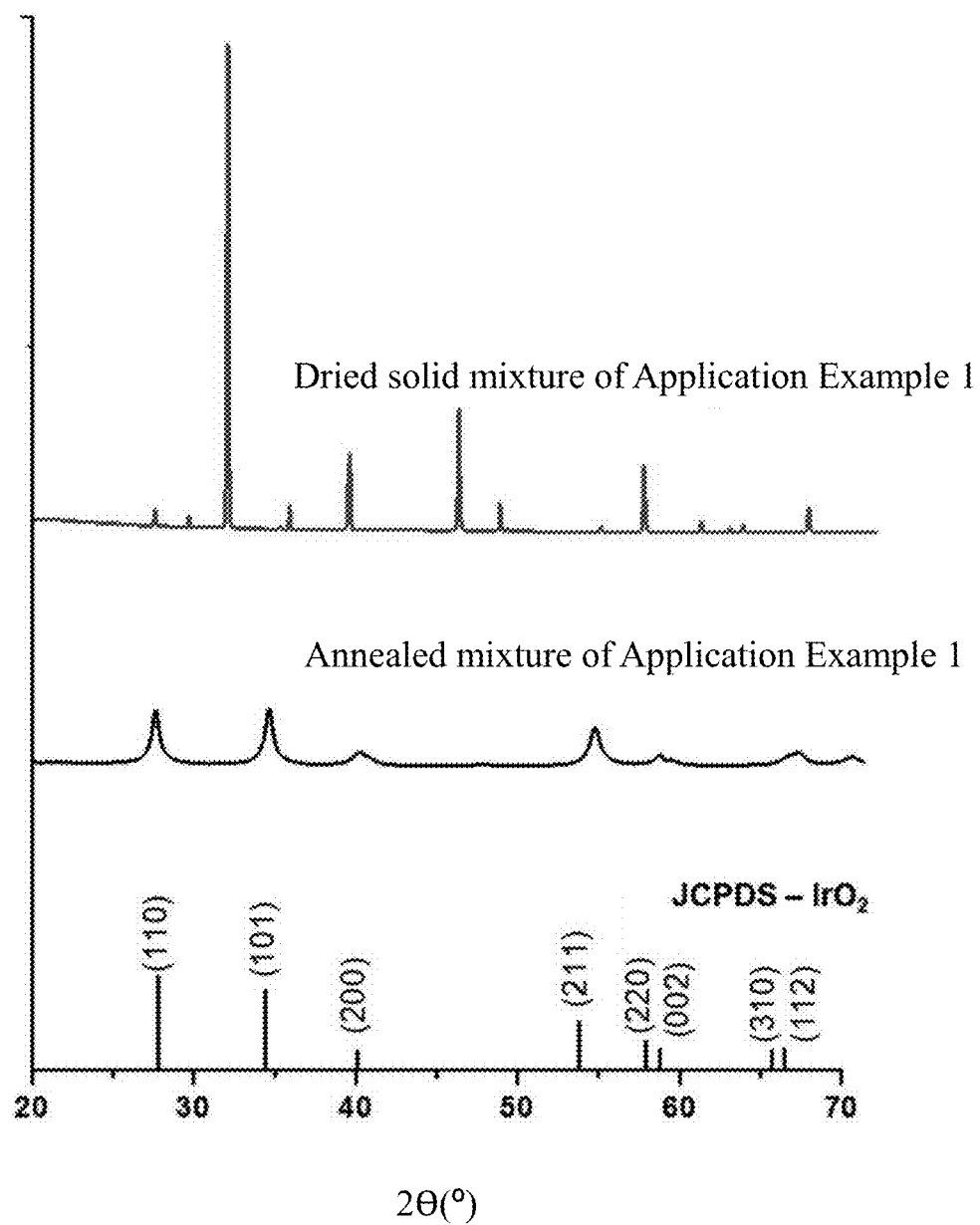
FIG. 1 is an X-ray diffraction diagram of a dried solid mixture and an annealed mixture obtained in Application Example 1, and rutile iridium dioxide (JCPDS card NO. 00-043-10192)

A method for making iridium oxide nanoparticles according to an embodiment of the disclosure includes steps a) to c).

In step a), an iridium salt is dissolved in a salt-dissolving solvent to obtain a salt-containing solution.

Step b) is implemented after step a). In step b), a complexing agent is mixed with the salt-containing solution to obtain a blend solution. The complexing agent includes a complexing compound which is for complexing iridium ions of the iridium salt, and which has a molar amount larger than that of the iridium salt.

Step c) is implemented after step b). In step c), an oxidating agent is added to the blend solution so as to permit oxidation of the iridium ions, to thereby obtain a product mixture. The oxidating agent includes an oxidant compound. A molar ratio of the complexing compound to the iridium salt is controlled in a predetermined range so as to permit the product mixture produced in step c) to include iridium oxide nanoparticles.

In certain embodiments, the salt-containing solution in step a) may include one or several kinds of the iridium salts, and one or several kinds of the salt-dissolving solvents. The iridium salt is, for example, but is not limited to, selected from a group consisting of $Na_3IrCl_6$, $K_3IrCl_6$, $IrCl_3$, $IrBr_3$, $Na_2IrCl_6$, $K_2IrCl_6$, $(NH_4)_2IrCl_6$, and combinations thereof. In an example, the iridium salt is $Na_3IrCl_6$, and has a concentration ranging from 0.1 mM to 1M in the salt-containing solution. The salt-dissolving solvent may be water or alcohol. The alcohol may be, but is not limited to, methanol, ethanol, propanol, etc. In an example, the salt-dissolving solvent is water.

In certain embodiments, the complexing agent in step b) may include one or several kinds of the complexing compounds. The complexing compound is, but is not limited to, selected from the group consisting of citric acid, malonic acid, succinic acid, oxalic acid, tartaric acid, EDTA, citrate, malonate, succinate, oxalate, tartrate, EDTA-2Na, and combinations thereof. In an example, the complexing compound is citric acid and has a concentration ranging from 0.6 mM to 7 M in the blending solution.

In certain embodiments, in step b), the molar ratio of the complexing compound to the iridium salt may be controlled to range from 70000:1 to 6:1. In an example, the molar ratio of the complexing compound to the iridium salt is 10:1.

In certain embodiments, the oxidating agent may include one or several kinds of the oxidant compounds. The oxidant compound is, but is not limited to, selected from the group consisting of $NaClO$, $NaClO_2$, $KClO$, $NaBrO_3$, $Ca(ClO)_2$, $H_2O_2$, and combinations thereof. In an example, the oxidant compound is $NaClO$.

In certain embodiments, a molar ratio of the oxidant compound to the iridium salt may range from 600:1 to 50:1. In an example, the molar ratio of the oxidant compound to the iridium salt is 132:1.

In certain embodiments, the product mixture produced in step c) has a pH ranging from 6 to 8. In an example, the product mixture produced in step c) has a pH of 7.

In certain embodiments, step c) is implemented in absence of heating.

In certain embodiments, the molar ratio of the complexing compound to the iridium salt is controlled in the predetermined range such that once the oxidating agent is added, the iridium oxide nanoparticles are produced within 10 minutes. In this case, the iridium oxide nanoparticles are stably suspended in the product mixture, and are less likely to congregate or precipitate. Therefore, the product mixture, which has uniform distribution of the iridium oxide nanoparticles, may be useful for making, e.g., a bio-ink.

In certain embodiments, the method may further includes a step b') between steps b) and c). In step b'), a stabilizing agent is added to stabilize the iridium ions in the blend solution at a pH ranging from 3 to 5. In an example, the blend solution in step b') has a pH of 4.

In certain embodiments, the stabilizing agent may include one or several kinds of compounds. The compound of the stabilizing agent is, but is not limited to, selected from NaOH, KOH, tetrabutylammonium hydroxide, $HNO_3$, and combinations thereof. In an example, the stabilizing agent includes NaOH.

In certain embodiments, the complexing compound is selected from the group consisting of citric acid, malonic acid, succinic acid, oxalic acid, tartaric acid, EDTA, and combinations thereof, and the stabilizing agent includes a compound selected from the group consisting of NaOH, KOH, tetrabutylammonium hydroxide, and combinations thereof.

In certain embodiments, the complexing compound is selected from the group consisting of citrate, malonate, succinate, oxalate, tartrate, EDTA-2Na, and combinations thereof, and the stabilizing agent includes $HNO_3$.

In certain embodiments, the method may further include a step d) after step c). In step d), a pH adjusting agent is added to adjust the product mixture to a pH value ranging from 1 to 13.

In certain embodiments, the pH adjusting agent is, but is not limited to, selected from the group consisting of NaOH, KOH, tetrabutylammonium hydroxide, $HNO_3$, and combinations thereof.

In certain embodiments, the method may further include a step e) after step c) or d). In step e), the iridium oxide nanoparticles are collected from the product mixture. The iridium oxide nanoparticles in step e) may be collected by, for example, centrifugation or filtration.

In certain embodiments, the method may further include a step f) after step e). In step f), the collected iridium oxide nanoparticles are heated so as to increase the particle size of the iridium oxide nanoparticles.

A bio-ink according to an embodiment of the disclosure includes the iridium oxide nanoparticles made by the above method, and a dispersant for dispersing the iridium oxide nanoparticles. The dispersant is, for example, water or an organic solvent, and the organic solvent may be alcohol or cyclohexanone.

The embodiments of the disclosure will now be explained in more detail below by way of the following examples and comparative examples. Those examples are intended for purposes of illustration only and are not intended to limit the scope of the present disclosure.

Example 1

A method for making iridium dioxide nanoparticles of Example 1 included steps a), b), b'), c), d), e), and f).

In step a), 14.2 mg sodium hexachloroiridate(III) hydrate ($Na_3IrCl_6 \cdot xH_2O$, Ir: 40.56 wt %, Strem Chemicals) was dissolved in 3 ml of deionized water (a salt-dissolving solvent) to obtain an orange/yellow salt-containing solution with a pH of 4.5. To ensure complete dissolution, the solution was left still for 24 hours. A concentration of the iridium salt in the salt-containing solution was 0.01 M.

In step b), 3 ml of a complexing agent (0.1 M citric acid solution including water and citric acid for complexing iridium ions) was mixed with the salt-containing solution to obtain a light yellow blend solution of pH 2.1. A molar ratio of the citric acid to the sodium hexachloroiridate(III) hydrate was 10:1.

In step b'), 0.15 ml of a stabilizing agent (1M sodium hydroxide solution including sodium hydroxide and water) was added to the light yellow blend solution to obtain a stabilized mixture of pH 4. The sodium hydroxide was provided for stabilizing the iridium ions.

In step c), at 25° C., 2 ml of an oxidating agent (a sodium hypochlorite solution including sodium hypochlorite (in the oxide form, 12 wt %) and water) was added to the stabilized mixture to obtain a blue product mixture of pH 7. A molar ratio of the sodium hypochlorite to the sodium hexachloroiridate (III) hydrate was 132:1. The sodium hypochlorite was provided for oxidation of the iridium ions. The blue product mixture had suspended iridium dioxide ($IrO_2$) nanoparticles having an average size of 3 nm. A large amount of bubbles were produced during oxidation reaction of the iridium ions, and when the bubbles disappeared, the iridium dioxide nanoparticles were formed. Step c) was accomplished within 3 minutes.

In step d), a pH adjusting agent (1M sodium hydroxide solution including sodium hydroxide and water) was added to the blue product mixture to obtain an adjusted mixture of pH 10.

In step e), the iridium dioxide nanoparticles in the adjusted mixture were centrifuged and collected using a high speed centrifuge.

In step f), the collected iridium dioxide nanoparticles were heated to increase the particle size of the iridium dioxide nanoparticles to 50 nm.

Example 2

The method for making iridium dioxide nanoparticles of Example 2 was similar to that of Example 1 except that, in Example 2, the molar ratio of the citric acid to the sodium hexachloroiridate (III) hydrate was 7:1. In step a), 3 ml of the salt-containing solution was prepared. In step b), 2.1 ml of the complexing agent (0.1 M citric acid solution) was added and the blend solution had pH of 3.28. In step b'), 0.23 ml of the stabilizing agent (1M sodium hydroxide solution) was added, and the stabilized mixture had pH of 3.82. In step c), the molar ratio of the sodium hypochlorite to the sodium hexachloroiridate (III) hydrate was 132:1. Once the oxidating agent (the sodium hypochlorite solution) was added, a large amount of bubbles were produced and the color of the mixture changed from brown to brownish green. When the bubbles disappeared, the product mixture (pH 7) was observed to have suspended iridium dioxide nanoparticles. Step c) was accomplished within 20 minutes.

Example 3

The method for making iridium dioxide nanoparticles of Example 3 was similar to that of Example 1 except that, in Example 3, the molar ratio of the citric acid to the sodium hexachloroiridate (III) hydrate was 70000:1, and the molar ratio of the sodium hypochlorite to the sodium hexachloroiridate (III) hydrate was 26:1. In step a), 0.6 ml of the salt-containing solution was prepared. In step b), 4.2 ml of the complexing agent (0.1 M citric acid solution) was added and the blend solution had pH of 3.79. In step b'), 0.44 ml of the stabilizing agent (1M sodium hydroxide solution) was added, and the stabilized mixture had pH of 3.79. In step c), 0.4 ml of the oxidating agent (the sodium hypochlorite solution) was added, and the product mixture (pH 7) was observed to be transparent and have suspended iridium dioxide nanoparticles.

Example 4

The method for making iridium dioxide nanoparticles of Example 4 was similar to that of Example 1 except that, in Example 4, the molar ratio of the citric acid to the sodium hexachloroiridate(III) hydrate was 20:1. In step a), 3 ml of the salt-containing solution was prepared. In step b), 6 ml of the complexing agent (0.1 M citric acid solution) was added and the blend solution had pH of 3.81. In step b'), 0.67 ml of the stabilizing agent (1M sodium hydroxide solution) was added, and the stabilized mixture had pH of 3.81. In step c), the molar ratio of the sodium hypochlorite to the sodium hexachloroiridate (III) hydrate was 132:1, and a large amount of bubbles were produced. When the bubbles disappeared, the product mixture (pH 7) was observed to be blue and have suspended iridium dioxide nanoparticles. Step c) was accomplished within 90 minutes.

Example 5 to Example 8

The methods for making iridium dioxide nanoparticles in Examples 5 to 8 were similar to that of Example 1 except that steps d) in Examples 5 to 8 were implemented by adding the 1M sodium hydroxide solution or a 1M nitric acid solution (including nitric acid and water) to adjust pH to 1, 3, 5, and 12, respectively.

Example 9

The method for making iridium dioxide nanoparticles of Example 9 was similar to that of Example 1 except that, in Example 9, the molar ratio of the citric acid to the sodium hexachloroiridate (III) hydrate was 6:1. In step a), 3 ml of the salt-containing solution was prepared. In step b), 1.8 ml of the complexing agent (0.1 M citric acid solution) was added and the blend solution had pH of 3.96. In step b'), 0.23 ml of the stabilizing agent (1M sodium hydroxide solution) was added, and the stabilized mixture had pH of 3.96. In step c), the molar ratio of the sodium hypochlorite to the sodium hexachloroiridate (III) hydrate was 132:1, and a large amount of bubbles were produced. When the bubbles disappeared, the product mixture (pH 7) was observed to be yellow green and have suspended iridium dioxide nanoparticles. Step c) was accomplished within 20 minutes.

Comparative Example 1

The method for making iridium dioxide nanoparticles of Comparative Example 1 was similar to that of Example 1 except that, in Comparative Example 1, the molar ratio of the citric acid to the sodium hexachloroiridate (III) hydrate was 1:1. In step a), 3.3 ml of the salt-containing solution was prepared, and a small silicon dioxide piece having an indium tin oxide layer thereon was disposed in the salt-containing solution. In step b), 3.3 ml of the complexing agent (0.01 M citric acid solution) was added. In step b'), 1 ml of the stabilizing agent (1M sodium hydroxide solution) was added. In step c), the molar ratio of the sodium hypochlorite to the sodium hexachloroiridate(III) hydrate was 132:1, and the product mixture was observed to be yellow green. In the product mixture, an iridium dioxide layer of about 70 nm, on which iridium dioxide nanoparticles with particle sizes ranging ranged from 250 nm to 400 nm were aggregated, was deposited on the indium tin oxide layer of the silicon dioxide piece. In addition, suspended iridium dioxide nanoparticles were not observed in the product mixture, and step c) was accomplished within 120 minutes.

Application Example 1

The product mixture obtained in step c) of Example 1 was dried at 60° C. for 48 hours to obtain a dried solid mixture. During drying, the sodium chloride and the sodium citrate in the product mixture precipitated. The dried solid mixture was grounded into powder and then annealed at 450° C. for 2 hours in an air atmosphere to obtain an annealed mixture. The annealed mixture was washed with water for dissolving the sodium chloride and the sodium citrate, followed by filtration to collect the iridium dioxide nanoparticles. The washing and filtration were repeated for several times. Thereafter, a bio-ink was prepared by mixing the collected iridium dioxide nanoparticles (0.5 wt %) with deionized water (99.5 wt %). The bio-ink was fed to an ink cartridge (Module: DMC 11610) of an ink-jet printer (Fujifilm, Module: DMP-2831), and then printed on an indium tin oxide substrate to form a pattern having the iridium dioxide nanoparticles. During printing, each drop of the bio-ink had a size of 10 pL, each printing dot had 40 pL of bio-ink, the lateral movement distance was 0.12 mm, the cartridge temperature was set to 25° C., and the temperature of the indium tin oxide substrate was set to 45° C.

Evaluation

X-Ray Diffraction Analysis

The dried solid mixture and the annealed mixture obtained in Application Example 1 were analyzed using an X-ray diffractometer, and the results are shown in FIG. 1.

Microscopy Analysis

Figure 2:
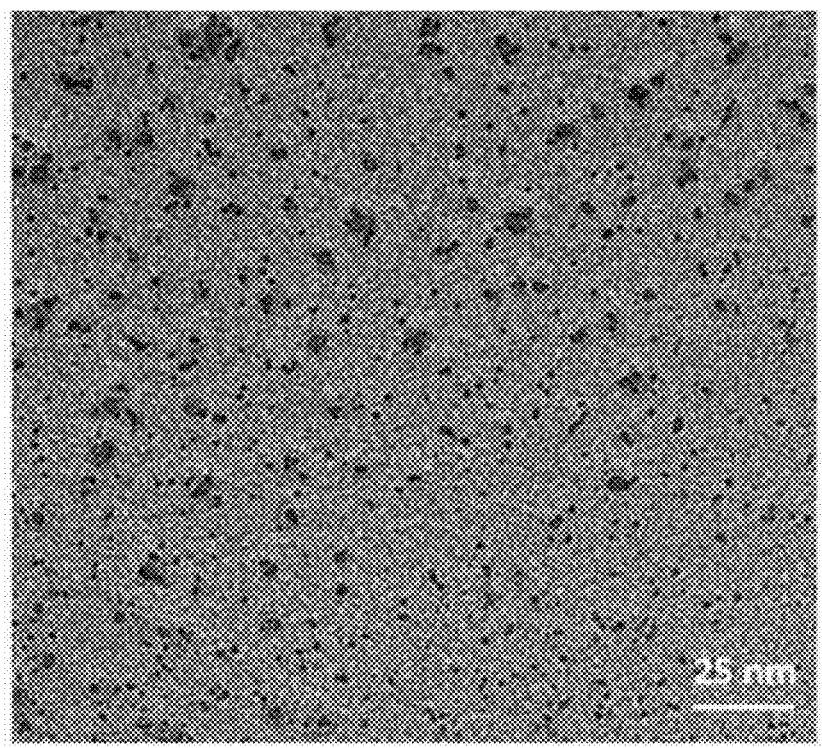
FIG. 2 is a transmission electron microscopy (TEM) image of iridium dioxide nanoparticles obtained in Application Example 1.
Figure 8:
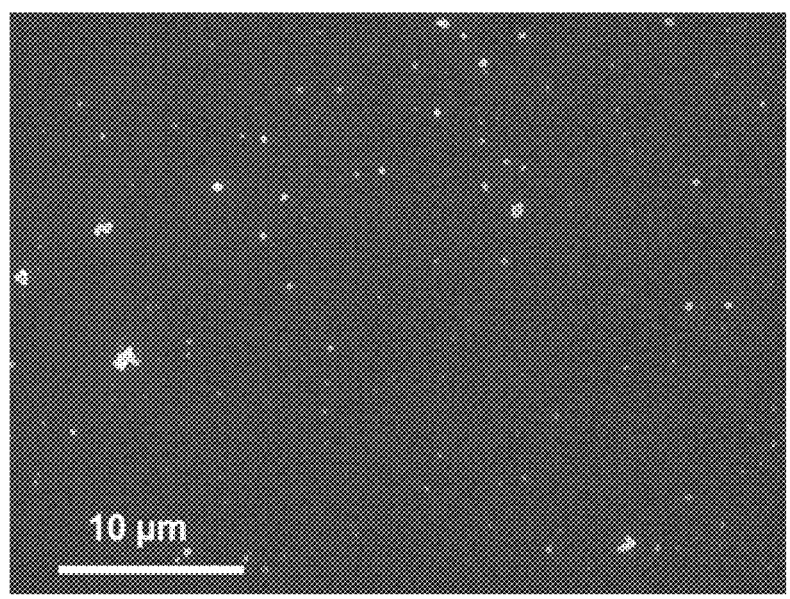
FIGS. 8 and 9 are scanning electron microscopy images for illustrating that no suspended iridium dioxide nanoparticles are obtained in Comparative Example 1.
Figure 9:
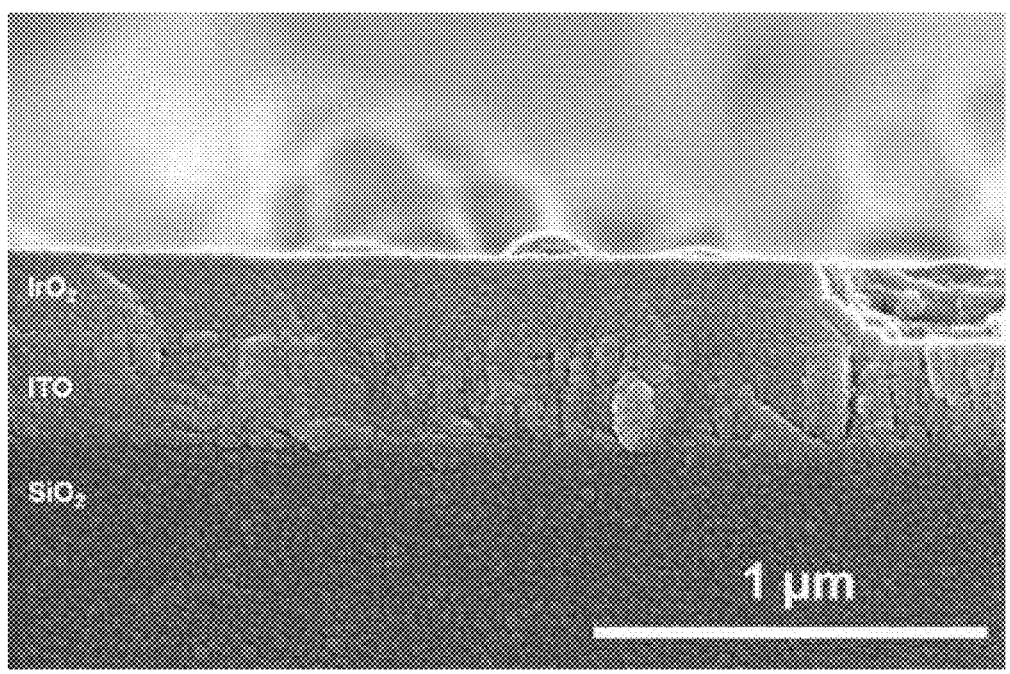

The dried solid mixture obtained in Application Example 1 was analyzed using a field emission transmission electron microscope (manufactured by JEOL Inc., Model: JEM-F200), and the result is shown in FIG. 2. In addition, the silicon dioxide piece obtained in step c) of Comparative Example 1 was also analyzed using a field emission scanning electron microscope (manufactured by Hitachi High-Technologies Corporation, Model: SU8010) and the result is shown in FIGS. 8 and 9.

UV-VIS Spectroscopy Analysis

Figure 3:
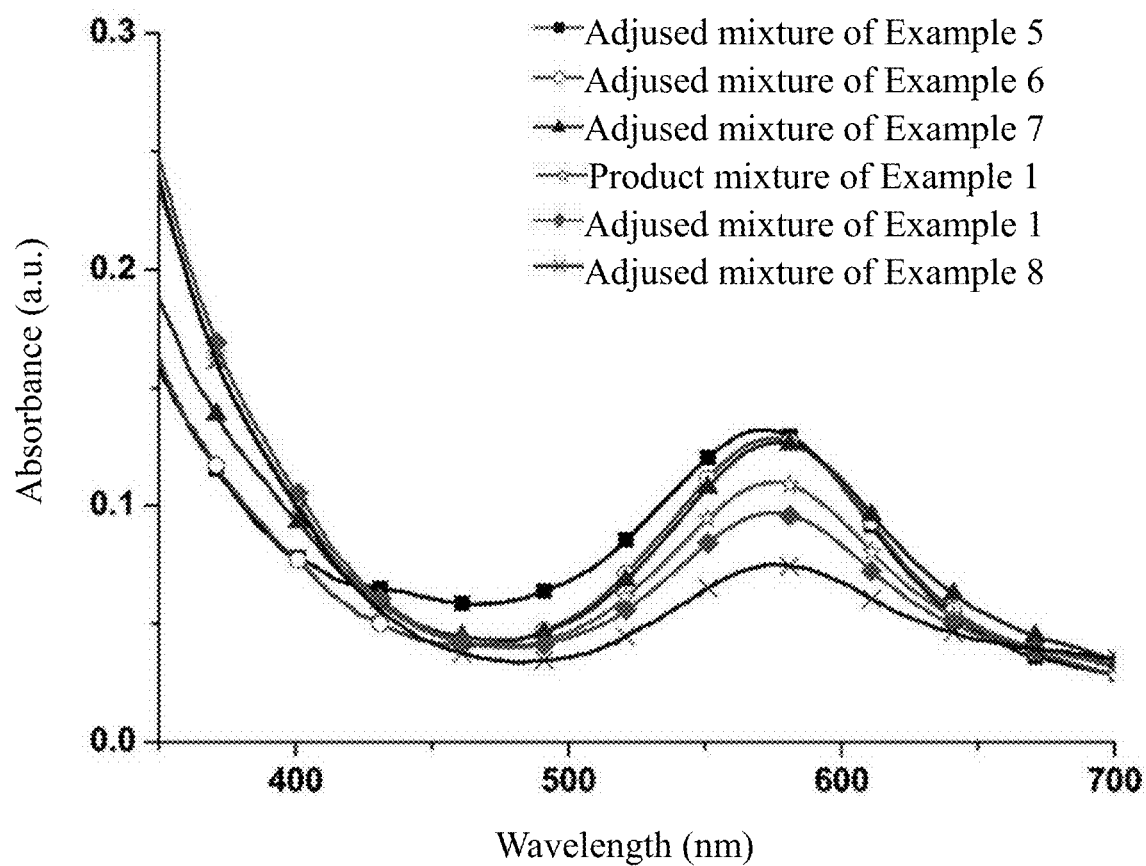
FIG. 3 presents UV-VIS absorbance spectra of adjusted mixtures obtained in Examples 1 and 5 to 8 and a product mixture of Example 1.

The adjusted mixtures obtained in step d) of Examples 1 and 5 to 8 were each 10 times diluted with water to have pH of 7.22, 9.54, 1.95, 3.45, 5.36, and 11.13, respectively. The product mixture obtained in step c) of Example 1 was also diluted 10 times with water. The diluted adjusted mixtures of Examples 1 and 5 to 8, and the diluted product mixture of Example 1 were analyzed using a UV-VIS spectrometer (manufactured by JASCO Inc., Model: V-730). The results are shown in FIG. 3.

Figure 4:
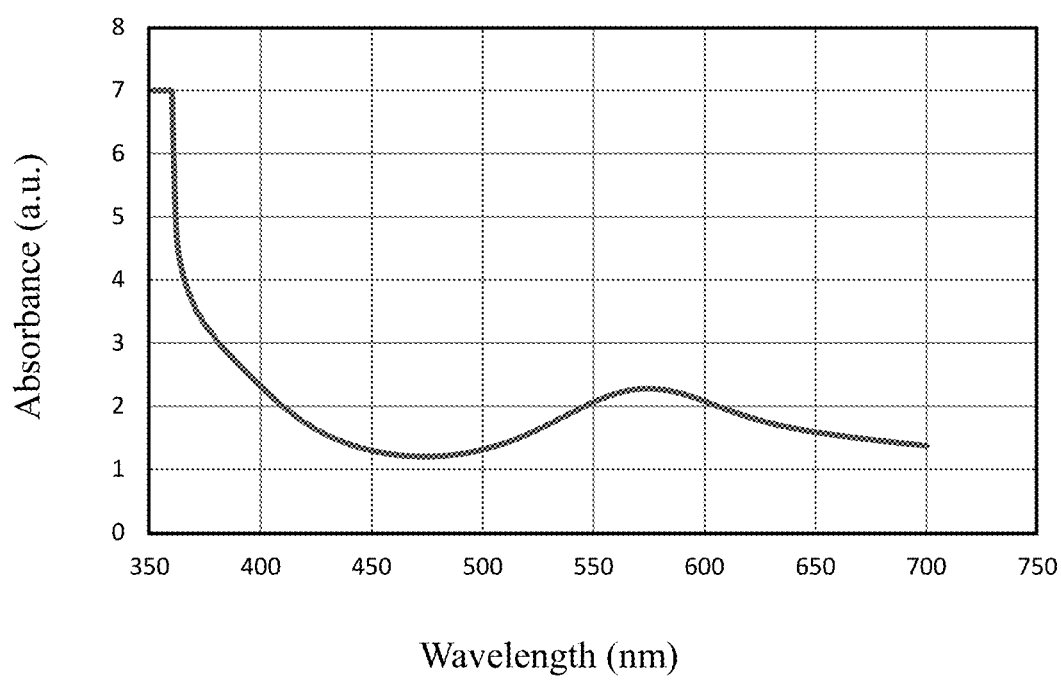
FIG. 4 presents a UV-VIS absorbance spectrum of an adjusted mixture obtained in Example 2.
Figure 5:
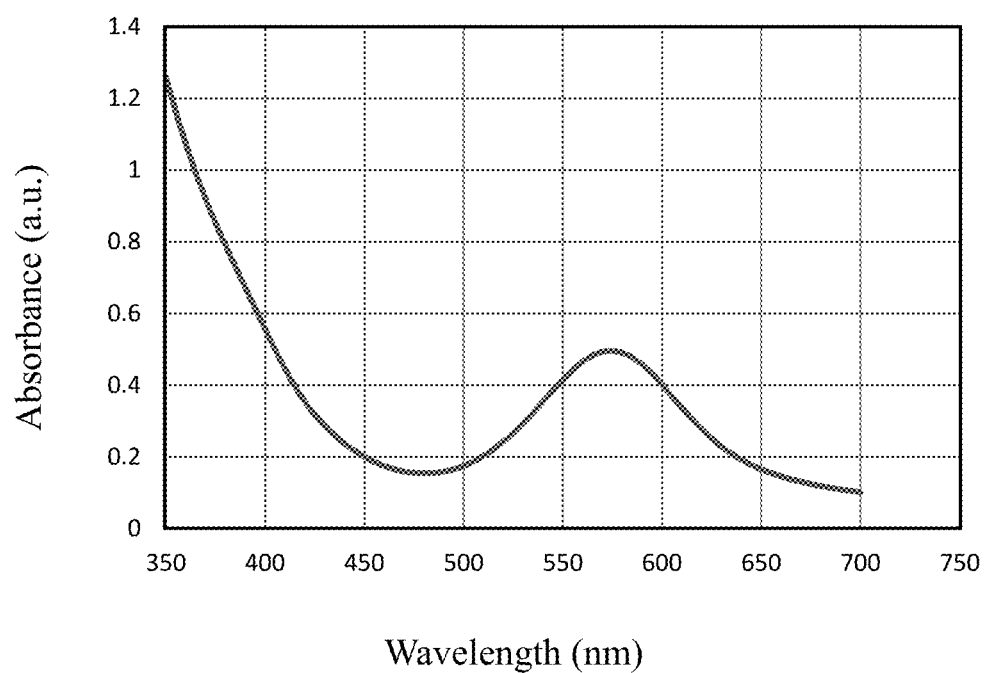
FIG. 5 presents a UV-VIS absorbance spectrum of an adjusted mixture obtained in Example 4.

The adjusted mixtures (pH 10) obtained in step d) of Examples 2 and 4 were each 10 times diluted with water, followed by analysis using the UV-VIS spectrometer. The results of the diluted adjusted mixtures of Examples 2 and 4 are shown in FIGS. 4 and 5, respectively.

Zeta Potential Analysis

Figure 6:
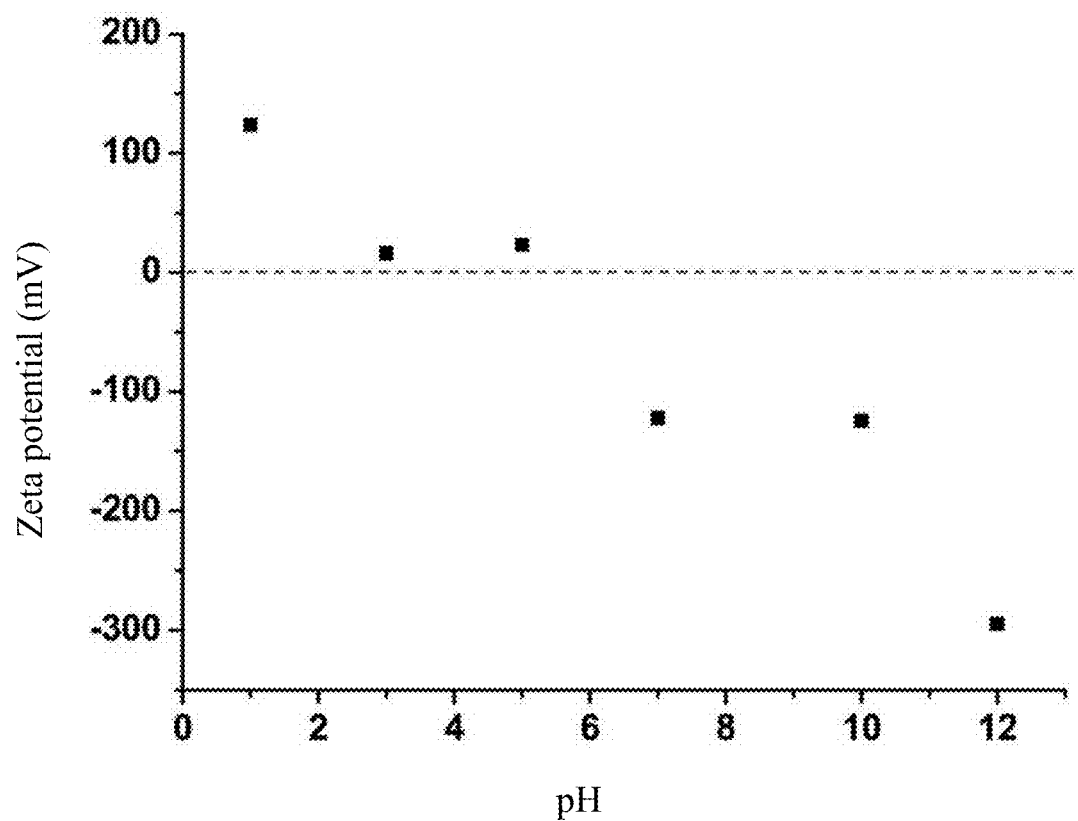
FIG. 6 is a diagram illustrating zeta potential versus pH for the product mixture obtained in Example 1.

The product mixture obtained in step c) of Example 1 and the adjusted mixtures obtained in step d) of Examples 1 and 5 to 8 were analyzed using a zeta potential measuring device (manufactured by Beckman Coulter GmbH., trade name: Delsa Nano C). The result is shown in FIG. 6.

Naked Eye Observation

The product mixture obtained in step c) of Example 1 and the adjusted mixtures obtained in step d) of Examples 1, 5, 7, and 8 at room temperature were observed to determine whether or not precipitation occurred.

The adjusted mixture (pH 10) obtained in step d) of Example 2, after standing at room temperature for 1 minute, 5 minutes, 25 minutes, 80 minutes, and 5 days, was observed to determine whether or not precipitation occurred.

The adjusted mixture (pH 10) obtained in step d) of Example 3, after standing at room temperature for 1 minute, 5 minutes, 40 minutes, and 240 minutes was observed to determine whether or not precipitation occurred.

The adjusted mixture (pH 10) obtained in step d) of Example 4, after standing at room temperature for 1 minute, 3 minutes, 20 minutes, 45 minutes, 90 minutes, and 5 days, was observed to determine whether or not precipitation occurred.

Stability Test

Six test samples from the product mixture obtained in step c) of Example 1 were respectively kept at 5° C., 10° C., 25° C., 45° C., 65° C., and 85° C. The test samples, after standing for 24 hours, 48 hours, 72 hours, and 96 hours were observed to determine whether or not precipitation occurred, and were each 10 times diluted with water, followed by analysis using the above-mentioned UV-VIS spectrometer to measure absorbance at 580 nm. The results of the absorbance for the test samples were shown in FIG. 7.

Result and Discussion

It can be observed from FIG. 1 that dried solid mixture and the annealed mixture obtained in Application Example 1 have some peaks coincident with the peaks of JCPDS card NO. 00-043-10192 (rutile $IrO_2$). Therefore, it is clear that the nanoparticles obtained are iridium dioxide.

Black spots shown in FIG. 2 are the iridium dioxide nanoparticles obtained in Application Example 1. The iridium dioxide nanoparticles are in a substantially ball form and were measured to have an average diameter of 3.5±0.4 nm.

In the absorbance spectrum shown in FIG. 3, it can be found that each of the adjusted mixtures of Examples 1 and 5 to 8 and the product mixture of Example 1 has an absorbance peak (the Ir—O—Ir bond) at 580 nm. In the absorbance spectra shown in FIGS. 4 and 5, each of the adjusted mixtures of Examples 2 and 4 has an absorbance peak (the Ir—O—Ir bond) at 580 nm. Therefore, it is further proved that the nanoparticles obtained in Examples are iridium dioxide.

It can be found in FIG. 6 that the values of the zeta potential are positive in the adjusted mixtures having pH of 1, 3, and 5. This is because the iridium dioxide nanoparticles in acid condition have too many protons thereon. The iridium dioxide nanoparticles in the product mixture (pH 7) or the adjusted mixture (pH 10) are end-capped with citrate ions, and thus, the values of the zeta potential are negative and stable in pH 7 and pH 10. The iridium dioxide nanoparticles in the adjusted mixture (pH 12) are end-capped with hydroxide ions, and thus the value of the zeta potential is more negative. It should be noted that although the zeta potential varies to a great extent (>20 mV) in a wide pH range (pH 1 to 12), the iridium dioxide nanoparticles in the wide pH range are stably suspended without precipitation.

In the naked eye observation, the product mixture of Example 1 and the adjusted mixtures of Examples 1, 5, 7, and 8 were all observed to be blue solutions, and without precipitation. The adjusted mixtures of Examples 2 to 4, standing for less than 5 days, were not observed to have precipitation.

Figure 7:
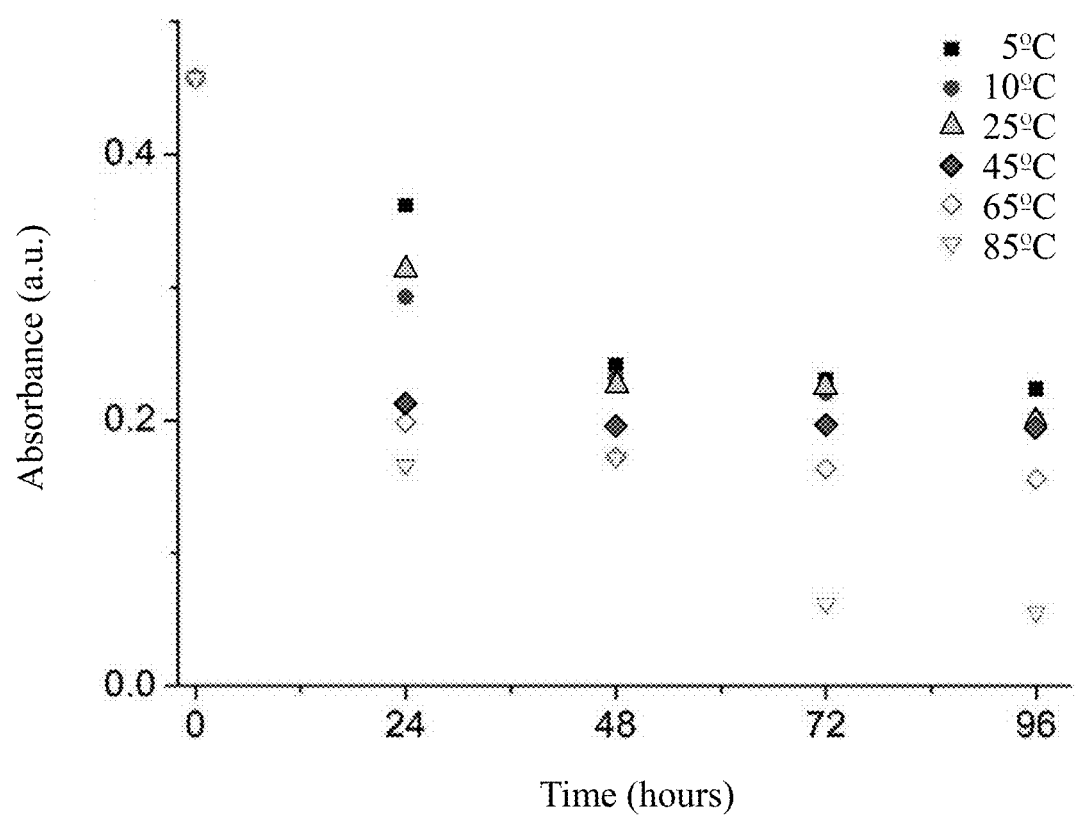
FIG. 7 is a diagram illustrating absorbance versus time for the product mixture obtained in Example 1 at different temperature.

In the stability test, it can be found in FIG. 7 that the test sample, after standing for 72 hours and 96 hours at 85° C., has a reduced absorbance, which may result from precipitation of the iridium dioxide nanoparticles. In the other conditions, the values of the absorbance for the test samples kept at 5° C., 10° C., 25° C., 45° C., and 65° C. are all above 0.1 a.u. Therefore, the product mixture obtained in Example 1 may have stable and uniform distribution of the iridium dioxide nanoparticles at a temperature lower than 85° C., and may be stored for a relatively long time.

Furthermore, the images shown in FIGS. 8 and 9 proved that when the molar ratio of the complexing compound (such as NaClO) to the iridium salt (such as $Na_3IrCl_6$) is not in the controlled range, the suspended iridium dioxide nanoparticles may not obtained.

In sum, in making iridium oxide nanoparticles, when a molar ratio of the complexing compound (such as NaClO) to the iridium salt (such as $Na_3IrCl_6$) is controlled in the predetermined range, the iridium oxide nanoparticles, rather than a layer of iridium oxide, are obtained.

In the description above, for the purposes of explanation, numerous specific details have been set forth in order to provide a thorough understanding of the embodiment (s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment (s), it is understood that this disclosure is not limited to the disclosed embodiment (s) but is intended to cover various arrangements included within the spirit and scope of the broadest interpretation so as to encompass all such modifications and equivalent arrangements.

What is claimed is:

1. A method for making iridium oxide nanoparticles, comprising steps of:
   a) dissolving an iridium salt in a salt-dissolving solvent to obtain a salt-containing solution;
   b) after step a), mixing a complexing agent with the salt-containing solution to obtain a blend solution, the complexing agent including a complexing compound for complexing iridium ions of the iridium salt, and which has a molar amount larger than that of the iridium salt; and
   c) after step b), adding an oxidating agent to the blend solution to permit oxidation of the iridium ions and obtain a product mixture, the oxidating agent including an oxidant compound,
   wherein a molar ratio of the complexing compound to the iridium salt is controlled in a predetermined range to permit the product mixture produced in step c) to include iridium oxide nanoparticles,
   wherein the salt-dissolving solvent in step a) is water, and
   wherein between steps b) and c), the method further comprises a step of b') adding a stabilizing agent to stabilize the iridium ions at a pH ranging from 3 to 5.

2. The method according to claim 1, wherein the molar ratio of the complexing compound to the iridium salt is controlled in the predetermined range such that once the oxidating agent is added, the iridium oxide nanoparticles are produced within 10 minutes.

3. The method according to claim 1, wherein the molar ratio of the complexing compound to the iridium salt is controlled to range from 70000:1 to 6:1.

4. The method according to claim 1, wherein a molar ratio of the oxidant compound to the iridium salt ranges from 600:1 to 50:1.

5. The method according to claim 1, wherein the product mixture produced in step c) has a pH ranging from 6 to 8.

6. The method according to claim 1, wherein step c) is implemented in the absence of heating.

7. The method according to claim 1, wherein the iridium salt is selected from the group consisting of $Na_3IrCl_6$, $K_3IrCl_6$, $IrCl_3$, $IrBr_3$, $Na_2IrCl_6$, $K_2IrCl_6$, $(NH_4)_2IrCl_6$, and combinations thereof.

8. The method according to claim 1, wherein
   the complexing compound is selected from the group consisting of citric acid, malonic acid, succinic acid, oxalic acid, tartaric acid, EDTA, and combinations thereof.

9. The method according to claim 8, wherein the stabilizing agent includes a compound selected from the group consisting of NaOH, KOH, tetrabutylammonium hydroxide, and combinations thereof.

10. The method according to claim 1, wherein the oxidant compound is selected from the group consisting of NaClO, $NaClO_2$, KClO, $NaBrO_3$, $Ca(ClO)_2$, $H_2O_2$, and combinations thereof.

11. The method according to claim 1, wherein the iridium salt is $Na_3IrCl_6$, the complexing compound is citric acid, the stabilizing agent includes NaOH, and the oxidant compound is NaClO.

12. The method according to claim 1, further comprising a step of d) after step c), adding a pH adjusting agent to adjust the product mixture to a pH value ranging from 1 to 13.

13. The method according to claim 12, wherein the pH adjusting agent is selected from the group consisting of NaOH, KOH, tetrabutylammonium hydroxide, $HNO_3$, and combinations thereof.

14. The method according to claim 1, further comprising a step of e) collecting the iridium oxide nanoparticles from the product mixture.

15. The method according to claim 14, further comprising a step of f) heating the collected iridium oxide nanoparticles so as to increase a particle size of the iridium oxide nanoparticles.

16. The method according to claim 1, when the complexing compound is selected from the group consisting of citrate, malonate, succinate, oxalate, tartrate, EDTA-2Na, and combinations thereof.

17. The method according to claim 16, the stabilizing agent includes $HNO_3$.

18. A method for making iridium oxide nanoparticles, comprising the steps of:
   a) dissolving an iridium salt in a salt-dissolving solvent to obtain a salt-containing solution;
   b) after step a), mixing a complexing agent with the salt-containing solution to obtain a blend solution, the complexing agent including a complexing compound which is for complexing iridium ions of the iridium salt, and which has a molar amount larger than that of the iridium salt; and
   c) after step b), adding an oxidating agent to the blend solution to permit oxidation of the iridium ions and obtain a product mixture, the oxidating agent including an oxidant compound,
   wherein a molar ratio of the complexing compound to the iridium salt is controlled in a predetermined range to permit the product mixture produced in step c) to include iridium oxide nanoparticles, and
   wherein the molar ratio of the complexing compound to the iridium salt is controlled in the predetermined range such that once the oxidating agent is added, the iridium oxide nanoparticles are produced within 10 minutes.

19. A method for making iridium oxide nanoparticles, comprising the steps of:
  a) dissolving an iridium salt in a salt-dissolving solvent to obtain a salt-containing solution;
  b) after step a), mixing a complexing agent with the salt-containing solution to obtain a blend solution, the complexing agent including a complexing compound which is for complexing iridium ions of the iridium salt, and which has a molar amount larger than that of the iridium salt; and
  c) after step b), adding an oxidating agent to the blend solution so as to permit oxidation of the iridium ions to obtain a product mixture, the oxidating agent including an oxidant compound,
  wherein a molar ratio of the complexing compound to the iridium salt is controlled in a predetermined range to permit the product mixture produced in step c) to include iridium oxide nanoparticles,
  wherein the salt-dissolving solvent in step a) is water, and
  wherein the product mixture produced in step c) has a pH ranging from 6 to 8.

* * * * *